(12) United States Patent
Lindorfer

(10) Patent No.: US 7,439,750 B2
(45) Date of Patent: Oct. 21, 2008

(54) SENSOR SYSTEM AND METHOD FOR ITS MANUFACTURE

(75) Inventor: Gerald Lindorfer, Haslach a.d. Muehl (AT)

(73) Assignee: E+E Elektronik GES.m.b.H., Engerwitzdorf (AT)

( * ) Notice: Subject to any disclaimer, the term of this patent is extended or adjusted under 35 U.S.C. 154(b) by 0 days.

(21) Appl. No.: 10/553,045

(22) PCT Filed: Mar. 3, 2004

(86) PCT No.: PCT/EP2004/003278

§ 371 (c)(1),
(2), (4) Date: Aug. 7, 2006

(87) PCT Pub. No.: WO2004/090523

PCT Pub. Date: Oct. 21, 2004

(65) Prior Publication Data

US 2007/0052429 A1 Mar. 8, 2007

(30) Foreign Application Priority Data

Apr. 12, 2003 (DE) ................. 103 16 933

(51) Int. Cl.
G01R 27/08 (2006.01)
G01R 27/26 (2006.01)
(52) U.S. Cl. .................... 324/696; 324/690
(58) Field of Classification Search ........... None
See application file for complete search history.

(56) References Cited

U.S. PATENT DOCUMENTS

| 4,720,451 A | 1/1988 | Shuto et al. | |
| 4,939,469 A * | 7/1990 | Ludwig et al. | 324/694 |
| 4,942,364 A | 7/1990 | Nishijima et al. | |
| 6,291,116 B1 | 9/2001 | Wolk et al. | |
| 6,483,324 B1 | 11/2002 | Mitter et al. | |
| 6,867,602 B2 * | 3/2005 | Davis et al. | 324/664 |
| 6,967,439 B2 * | 11/2005 | Cok et al. | 313/512 |
| 7,028,531 B2 * | 4/2006 | Nikolaus | 73/29.05 |

FOREIGN PATENT DOCUMENTS

| EP | 0 329 436 | 8/1989 |
| EP | 0 343 593 | 11/1989 |
| EP | 1 046 030 | 10/2000 |
| RU | 2 143 678 | 12/1999 |
| SU | 559130 | 12/1981 |
| WO | 01/58731 | 8/2001 |

OTHER PUBLICATIONS

Database WPI, Section EI, Week 198227, Derwent Publications Ltd., GB, Class S01, AN 1982-J0918E, XP002281382.

* cited by examiner

Primary Examiner—Vincent Q. Nguyen
Assistant Examiner—Jeff Natalini
(74) Attorney, Agent, or Firm—Kenyon & Kenyon LLP

(57) ABSTRACT

A sensor system includes a thin-film sensor provided with at least one contact area on the surface thereof, and a printed circuit board provided with at least one contact pad on the surface thereof. The thin-film sensor is arranged in relation to the surface of the printed circuit board such that the surface of the thin-film sensor opposes the surface of the printed circuit board. In order to transmit sensor currents from the thin-film sensor to the printed circuit board, a conductive glue adheres to both the contact area of the thin-film sensor and to the contact pad on the surface of the printed circuit board.

10 Claims, 3 Drawing Sheets

X - X

SENSOR SYSTEM AND METHOD FOR ITS MANUFACTURE

FIELD OF THE INVENTION

The present invention relates to a sensor system, e.g., for determining the relative humidity in air, and to a method for manufacturing such a sensor system.

BACKGROUND INFORMATION

Such sensor systems are often used for determining the relative humidity, for instance, in automotive air conditioners, in household appliances or in copier machines, and are consequently used in great quantities. As a cost-effective type of construction for the sensors used therein, so-called thin-film sensors are often used, whose functioning method is based, for example, on a capacitive measuring principle. The thin-film sensors are usually produced in planar fashion, i.e., all active films or layers as well as the contacting areas of the thin-film sensors are accommodated on one surface of the thin-film sensors. Generally, no coatings are then located on the back side of such thin-film sensors.

To manufacture a functional sensor system in as automated a manner as possible, printed circuit boards are fitted with these sensors and appropriately electrically contacted.

European Published Patent Application No. 1 046 030 describes a sensor system of this kind, the sensitive region of the sensor being disposed at an opening in the printed circuit board. This type of construction may have the disadvantage that, during operation of the sensor system, both sides of the printed circuit board are constantly exposed to the humidity to be measured. Moreover, additional production costs may result from the provision of the opening in the printed circuit board.

U.S. Pat. No. 4,942,364 describes a resistively acting moisture sensor, in which the moisture-dependent electrical resistance of a suitably prepared non-woven material is determined. This moisture sensor has two connecting wires for insertion into an electric circuit. The connecting wires are bonded to the non-woven material with the aid of a conductive adhesive. Such sensors may have the disadvantage that they are not, or are just barely, suitable for automatic assembly on a printed circuit board.

SUMMARY

An example embodiment of the present invention may provide a sensor system which may be producible with low manufacturing expenditure, and which may exhibit great robustness, as well as good measuring accuracy. An example embodiment of the present invention may provide a cost-effective and reliable method for manufacturing a sensor system of this kind.

According to an example embodiment of the present invention, the contacting area of a thin-film sensor is electrically connected to a contact pad on a printed circuit board using a conductive adhesive. In so doing, the sensor is placed relative to a surface of the printed circuit board such that the contacting area is disposed on a surface of the thin-film sensor facing away from the specified surface of the printed circuit board.

As conductive adhesive, adhesives are considered here which have a comparatively low electrical bulk resistance (e.g., less than $10^{-1}$ Ωcm, e.g., less than $10^{-2}$ Ωcm). Conductive adhesives may be used which are filled with electroconductive particles and have a proportion of filler of more than 50% by weight, e.g., more than 66% by weight.

In an example embodiment of the present invention, provided between the thin-film sensor and the printed circuit board may be a mounting adhesive which, on one hand, may simplify the mounting operation and may increase the operational reliability of the method, and on the other hand, also may ensure good thermal coupling of the thin-film sensor to the printed circuit board. In this connection, it may be provided that the mounting adhesive exhibits high thermal conductivity, e.g., greater than 0.3 W/(m·K). The mounting adhesive may have thermal conductivity greater than, e.g., 0.5 W/(m·K).

According to an example embodiment of the present invention, a sensor system includes: a thin-film sensor including a surface having at least one contact area; a printed circuit board including a surface having at least one contact pad, the thin-film sensor arranged relative to the surface of the printed circuit board such that the surface of the thin-film sensor faces away from the surface of the printed circuit board; and a conductive adhesive adapted to transmit sensor currents from the thin-film sensor to the printed circuit board, the conductive adhesive adhering to the contact area of the thin-film sensor and the contact pad on the surface of the printed circuit board.

The thin-film sensor may be arranged as one of (a) a humidity sensor and (b) a moisture sensor.

The thin-film sensor may be adapted to operate on a capacitive measuring principle.

The thin-film sensor may include two contact areas, each contact area joined by the conductive adhesive to a corresponding contact pad of the printed circuit board.

The sensor system may include a mounting adhesive arranged at least in one partial area between the thin-film sensor and the printed circuit board.

A thermal conductivity of the mounting adhesive may be greater than 0.3 W/(m·K).

According to an example embodiment of the present invention, a method for manufacturing a sensor system includes: placing a thin-film sensor relative to a surface of a printed circuit board such that a surface of the thin-film sensor on which a contact area is arranged is facing away from the surface of the printed circuit board; and bonding the thin-film sensor to the printed circuit board such that the contact area of the thin-film sensor is electrically connected by a conductive adhesive to a contact pad on the surface of the printed circuit board.

The method may include applying a mounting adhesive on one of (a) the surface of the printed circuit board and (b) the surface of the thin-film sensor prior to the placing step.

According to an example embodiment of the present invention, a sensor system includes: thin-film sensing means including a surface having at least one contact area; printed circuit board means including a surface having at least one contact pad, the thin-film sensing means arranged relative to the surface of the printed circuit board means such that the surface of the thin-film sensing means faces away from the surface of the printed circuit board means; and conductive adhering means for transmitting sensor currents from the thin-film sensing means to the printed circuit board means, the conductive adhering means adhering to the contact area of the thin-film sensing means and the contact pad on the surface of the printed circuit board means.

Further details and aspects of example embodiments of the present invention are described below in the following description with reference to the appended Figures.

DETAILED DESCRIPTION

Figure 1:
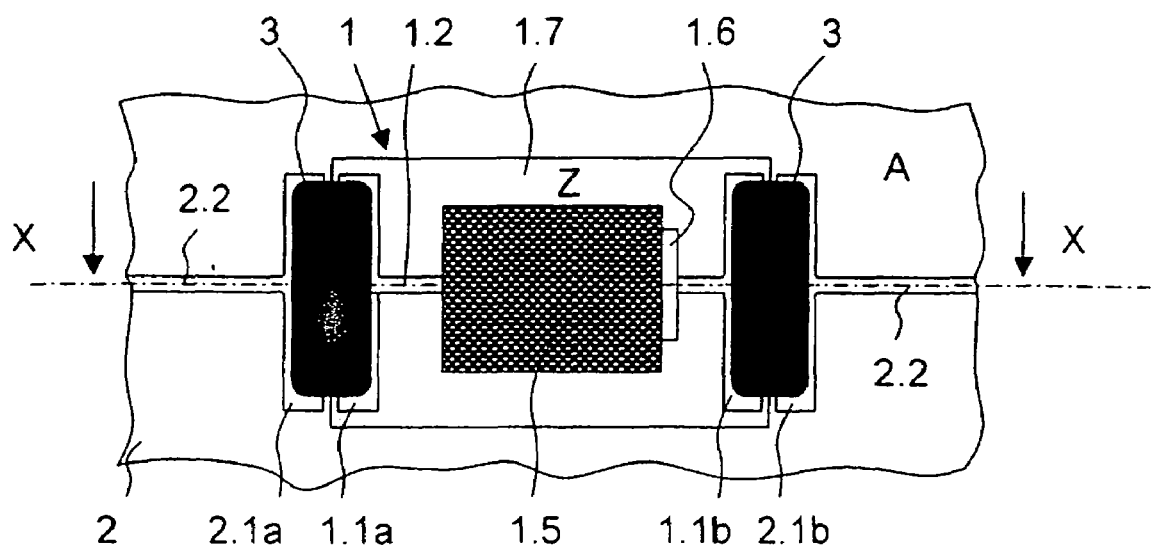
FIG. 1 is a top view of a sensor system according to an example embodiment of the present invention.

FIG. 1 is a top view of a sensor system according to an example embodiment of the present invention. The sensor system includes a thin-film sensor 1 and a printed circuit board 2, of which only a segment is illustrated.

Figure 2:
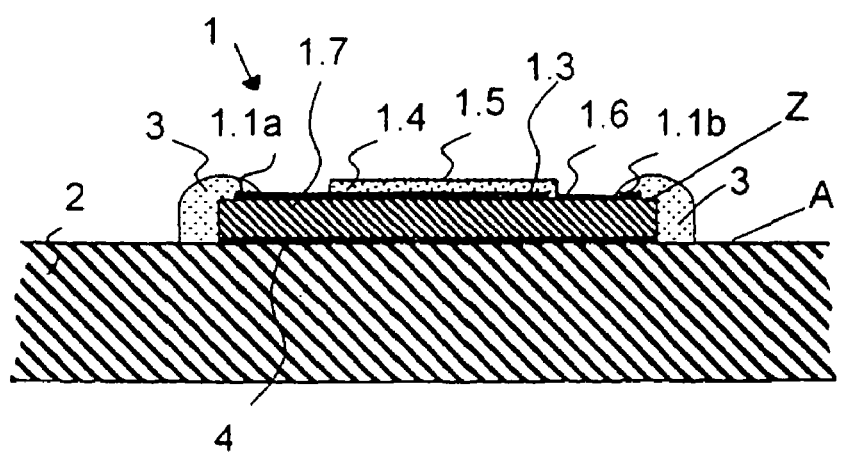
FIG. 2 is a cross-sectional view through the sensor system illustrated in FIG. 1 taken along the line X-X.

Thin-film sensor 1 is used for measuring the relative air humidity, and is based on a capacitive functional principle. Thin-film sensor 1 includes a substrate 1.7, on whose surface Z a base electrode 1.3 (see FIG. 2), made of gold in the example illustrated, is applied. In the exemplary embodiment illustrated, substrate 1.7 is made of glass. Base electrode 1.3 is electrically connected via a conductor track 1.2 to a contacting area 1.1a. Both conductor track 1.2 and contacting area 1.1a are located on surface Z of substrate 1.7. A moisture-sensitive or humidity-sensitive polymer 1.4 is applied over base electrode 1.3 in a sensitive region of thin-film sensor 1. Applied on this moisture-sensitive polymer 1.4 is a porous moisture electrode 1.5 which is in electrical contact with a further contacting area 1.1b on substrate 1.7 via a connecting electrode 1.6. Thus, on one hand, thin-film sensor 1 has surface Z having the sensitive region and contacting areas 1.1a, 1.1b, and on the other hand, has a passive side or back side opposite surface Z, on which no coating of substrate 1.7 whatsoever was carried out.

Printed circuit board 2 has a surface A on which conductor tracks 2.2 and contact pads 2.1a, 2.1b, e.g., in the form of thin, electroconductive copper layers, are applied. Thin-film sensor 1 is placed in the sensor system relative to surface A of printed circuit board 2 such that surface Z of thin-film sensor 1, which also has the sensitive region, is facing away from surface A of printed circuit board 2. That is to say, surface A of the printed circuit board and surface Z of thin-film sensor 1 are thus aligned essentially parallel to each other, but are located in different geometric planes.

A layer formed by a mounting adhesive 4 is located in the region between thin-film sensor 1 and printed circuit board 2. Mounting adhesive 4 includes a polymer matrix and fillers, silver particles in the example illustrated, so that its thermal conductivity at, e.g., 0.75 W/(m·K), may be comparatively great.

To transmit sensor currents from thin-film sensor 1 to printed circuit board 2, contacting area 1.1a of thin-film sensor 1 and contact pad 2.1a of printed circuit board 2 are electrically and mechanically interconnected by a conductive adhesive 3. Conductive adhesive 3 thus adheres both to contacting area 1.1a of thin-film sensor 1 and to contact pad 2.1a of printed circuit board 2, so that electrical voltages or currents are transmittable via conductive adhesive 3.

In this type of sensor, the change in capacitance of the sensitive region as a result of water adsorption of moisture-sensitive polymer 1.4 is used as a measured quantity. The resulting currents conducted via conductive adhesive 3 are then evaluated on printed circuit board 2.

Figure 3A:
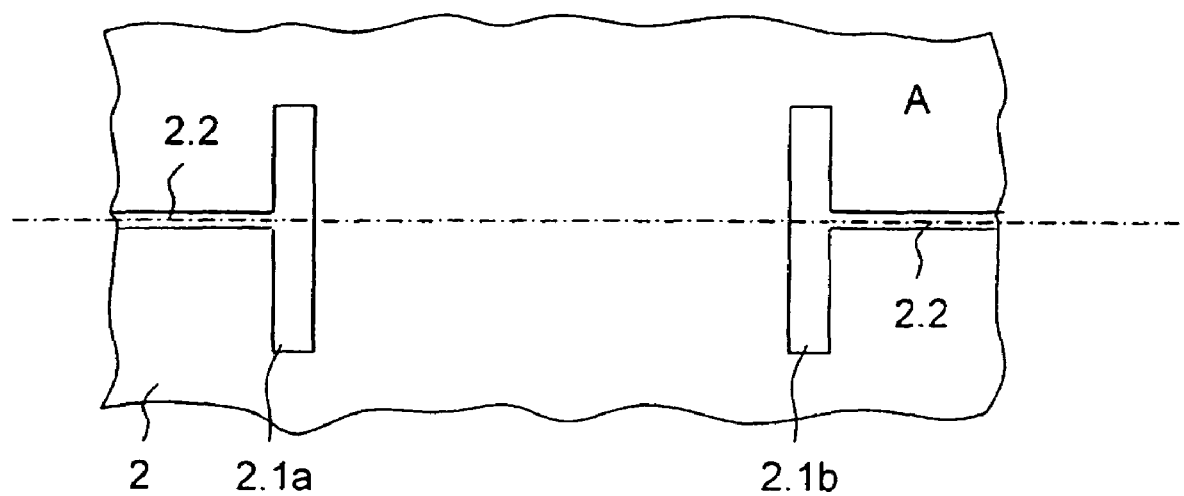
FIGS. 3a to 3d are top views of the sensor system after different manufacturing steps for illustrating a manufacturing method.

To manufacture the sensor system, as illustrated in FIG. 3a, first of all a printed circuit board 2 is made available, on which conductor tracks 2.2 and contact pads 2.1a, 2.1b are already applied on surface A.

Figure 3B:
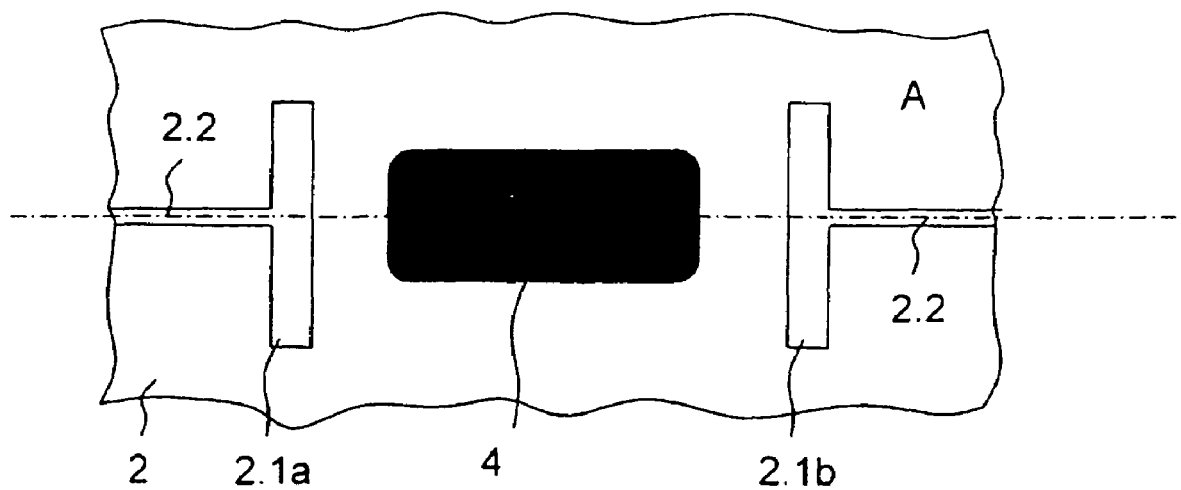

After that, in a first step S1, mounting adhesive 4 is applied on surface A of printed circuit board 2 in the region of the later contact area, thus here between the two contact pads 2.1a, 2.1b (FIG. 3b). Immediately after the application of mounting adhesive 4, the area moistened by mounting adhesive 4 is smaller than the area of substrate 1.7 of thin-film sensor 1.

Figure 3C:
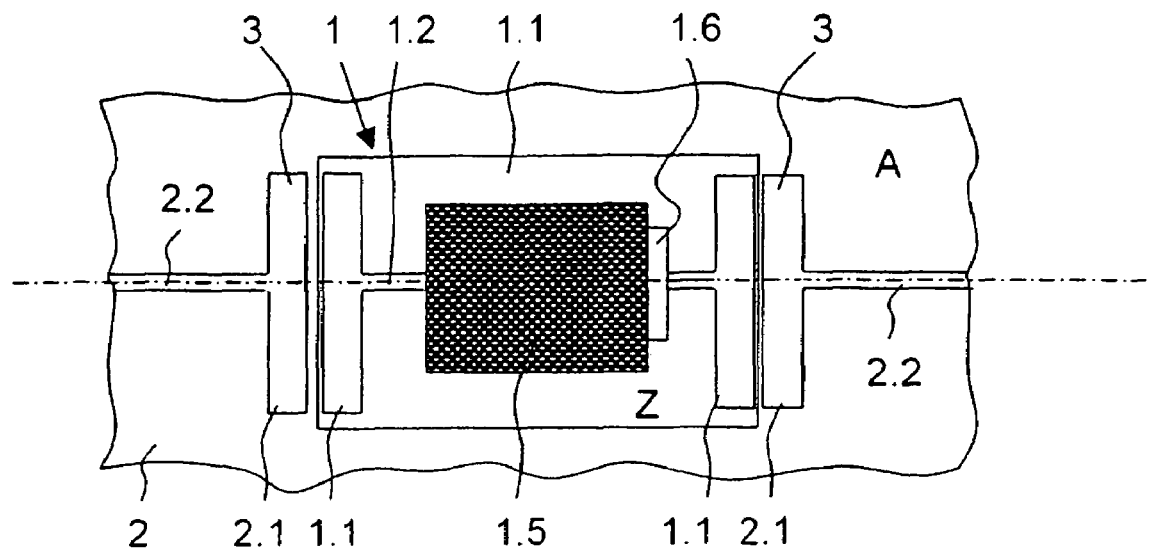

In a further step S2, as illustrated in FIG. 3c, thin-film sensor 1 is placed relative to printed circuit board 2. In so doing, thin-film sensor 1 is arranged such that surface Z of thin-film sensor 1, on which contacting areas 1.1 are arranged, is facing away from surface A of printed circuit board 2. In other words, the passive, non-sensitive side, thus, the back side of thin-film sensor 1 is joined, e.g., adhered, to printed circuit board 2. The amount of mounting adhesive 4 is apportioned in step S1 such that, after thin-film sensor 1 has been placed on printed circuit board 2, no mounting adhesive 4 is pressed over the edge of thin-film sensor 1, i.e., no mounting adhesive 4 emerges laterally from the joint gap or, for example, covers contact pads 2.1a, 2.1b as a result of pressing thin-film sensor 1 onto printed circuit board 2. It may thus be ensured that after step S2, the position of thin-film sensor 1 on printed circuit board 2 is fixed.

Figure 3D:
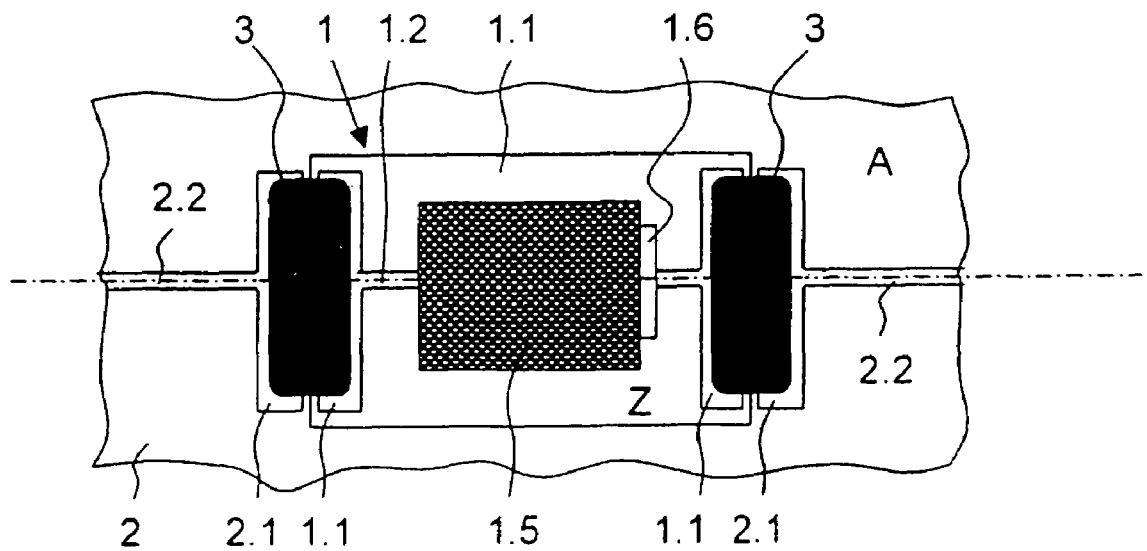

In the following step S3, a conductive adhesive 3 is applied at a first adhesive location onto contact pad 2.1a and contacting area 1.1a. The volume of conductive adhesive 3 at this adhesive location is apportioned such that conductive adhesive 3 touches both contacting area 1.1a and contact pad 2.1a, and after conductive adhesive 3 has hardened, adheres to these two locations. In this manner, an electrical connection is produced between contact pad 2.1a and contacting area 1.1a. Since contact pad 2.1a and contacting area 1.1a are in two different geometric areas parallel to each other, conductive adhesive 3 is disposed around an edge of thin-film sensor 1. Analogously, contact pad 2.1b and contacting area 1.1b are interconnected by conductive adhesive 3 at a second adhesive location, so that after step S3, a sensor system as illustrated in FIG. 3d may be provided.

On one hand, the use of a mounting adhesive 4 may mechanically relieve the adhesive bond of conductive adhesive 3. On the other hand, the layer of mounting adhesive 4 may ensure good thermal coupling of thin-film sensor 1 to printed circuit board 2, e.g., since, as already mentioned, mounting adhesive 4 may exhibit high thermal conductivity. This good thermal coupling may be particularly advantageous when a temperature sensor is arranged on printed circuit board 2, so that virtually no temperature gradient may exist between the temperature sensor and thin-film sensor 1, which may be of particular significance for the measuring quality, e.g., when measuring the dew point.

Due to the type of construction described, the sensor system may be used such that only one surface of printed circuit board 2, e.g., surface A, is exposed to the moist air. Therefore, this aspect may provide for manufacturing such printed circuit boards 2 more cost-effectively, and may increase the robustness of a sensor system of this kind.

What is claimed is:

1. A sensor system, comprising:
   a thin-film sensor including a first surface, the first surface having at least two contact areas;
   a printed circuit board including a second surface, the second surface having at least two contact pads, the thin-film sensor arranged relative to the second surface of the printed circuit board such that the first surface of the thin-film sensor having the at least two contact areas faces away from the second surface of the printed circuit board having the at least two contact pads;

a conductive adhesive adapted to transmit sensor currents from the thin-film sensor to the printed circuit board, the conductive adhesive adhering to the contact areas of the thin-film sensor and the contact pads on the second surface of the printed circuit board, each contact area joined by the conductive adhesive to a corresponding contact pad of the printed circuit board; and a mounting adhesive applied on the second surface of the printed circuit board in between the contact pads and arranged at least in one partial area between the thin-film sensor and the second surface of the printed circuit board.

2. The sensor system according to claim 1, wherein the thin-film sensor is arranged as one of (a) a humidity sensor and (b) a moisture sensor.

3. The sensor system according to claim 1, wherein the thin-film sensor is adapted to operate on a capacitive measuring principle.

4. The sensor system according to claim 1, wherein a thermal conductivity of the mounting adhesive is greater than 0.3 W/(m·K).

5. The sensor system according to claim 1, wherein the first surface of the thin-film sensor includes exactly two contact areas, and the second surface of the printed circuit board includes exactly two contact pads.

6. A method for manufacturing a sensor system, comprising:

applying a mounting adhesive on one of (a) a surface of a printed circuit board and (b) a surface of a thin-film sensor;

placing the thin-film sensor relative to the surface of the printed circuit board such that a surface of the thin-film sensor on which contact areas are arranged is facing away from the surface of the printed circuit board and such that the mounting adhesive is in arranged between at least two contact pads arranged on the surface of the printed circuit board and at least in one partial area between the thin-film sensor and the surface of the printed circuit board; and bonding the thin-film sensor to the printed circuit board such that the contact areas of the thin-film sensor are electrically connected by a conductive adhesive to the contact pads on the surface of the printed circuit board.

7. The method according to claim 6, wherein the mounting adhesive is applied in the applying step prior to the placing step.

8. The method according to claim 6, wherein the surface of the thin-film sensor includes exactly two contact areas, and the surface of the printed circuit board includes exactly two contact pads.

9. A sensor system, comprising:

thin-film sensing means including a first surface, the first surface having at least two contact areas;

printed circuit board means including a second surface, the second surface having at least two contact pads, the thin-film sensing means arranged relative to the second surface of the printed circuit board means such that the first surface of the thin-film sensing means having the at least two contact areas faces away from the second surface of the printed circuit board means having the at least two contact pads;

conductive adhering means for transmitting sensor currents from the thin-film sensing means to the printed circuit board means, the conductive adhering means adhering to the contact areas of the thin-film sensing means and the contact pads on the second surface of the printed circuit board means, each contact area joined by the conductive adhering means to a corresponding contact pad of the printed circuit board means; and mounting adhering means applied on the second surface of the printed circuit board means in between the contact pads and arranged at least in one partial area between the thin-film sensing means and the second surface of the printed circuit board means.

10. The sensor system according to claim 9, wherein the first surface of the thin-film sensing means includes exactly two contact areas, and the second surface of the printed circuit board means includes exactly two contact pads.

* * * * *